United States Patent [19]

Gershman et al.

[11] 4,325,706
[45] Apr. 20, 1982

[54] AUTOMATED DETECTION OF PLATELETS AND RETICULOCYTES IN WHOLE BLOOD

[75] Inventors: Russell J. Gershman; W. Peter Hansen, both of Middleboro; Alan M. Hochberg, Cambridge; J. Garland O'Connell, Waltham, all of Mass.

[73] Assignee: Ortho Diagnostic Systems Inc., Raritan, N.J.

[21] Appl. No.: 178,486

[22] Filed: Aug. 15, 1980

[51] Int. Cl.³ ............... G01N 1/30; G01N 21/25; G01N 33/50
[52] U.S. Cl. ............... 23/230 B; 356/39; 424/3
[58] Field of Search ............... 23/230 B; 422/68, 81, 422/82; 356/39, 40; 424/3

[56] References Cited

U.S. PATENT DOCUMENTS

| | | | |
|---|---|---|---|
| 3,781,112 | 12/1973 | Groner et al. | 356/39 |
| 3,883,247 | 5/1975 | Adams | 356/39 |
| 3,896,307 | 7/1975 | Trowe | 356/39 |
| 3,919,530 | 11/1975 | Cheng | 23/230 B |
| 3,989,382 | 11/1976 | Kent et al. | 23/230 B |
| 4,000,417 | 12/1976 | Adkisson et al. | 356/39 |
| 4,219,440 | 8/1980 | Runck et al. | 356/39 |

Primary Examiner—Ronald Serwin
Attorney, Agent, or Firm—Audley A. Ciamporcero, Jr.

[57] ABSTRACT

A sample of whole blood is stained with an acridine orange reagent, and is analyzed rapidly, a cell at a time, in a flow cytometry system having a sample stream dimension in the range of expected red cell dimensions. Red florescence and forward scatter data is utilized first to discriminate a cell from noise, and then to distinguish platelets from reticulocytes and red cells. The red cell and reticulocyte data is subjected to a correction such as rotational coordinate shift, and the shifted data are, by means of statistical procedures, utilized to determine threshold criteria separating red cells from reticulocytes, and to enumerate the cells on that basis.

7 Claims, 12 Drawing Figures

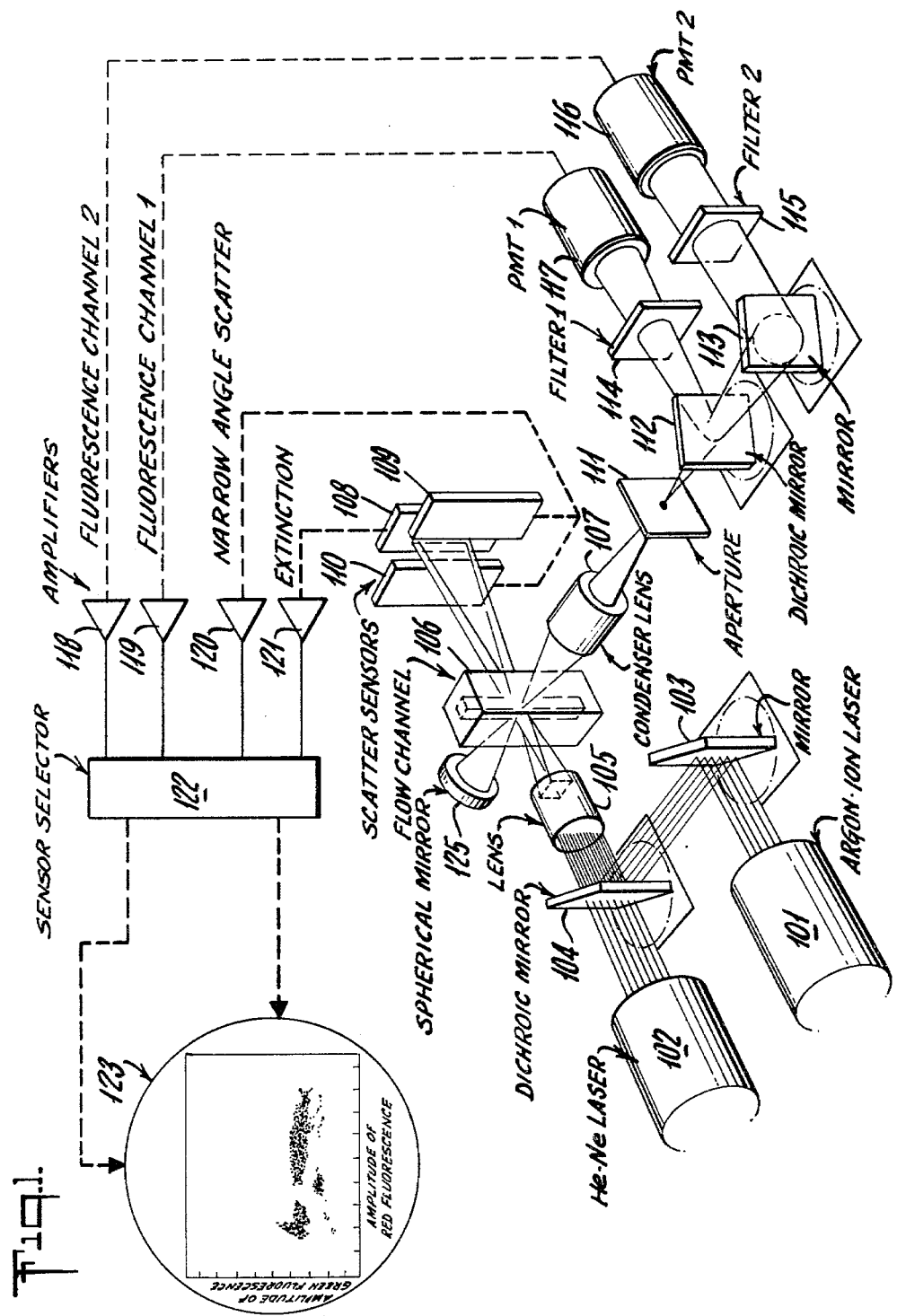

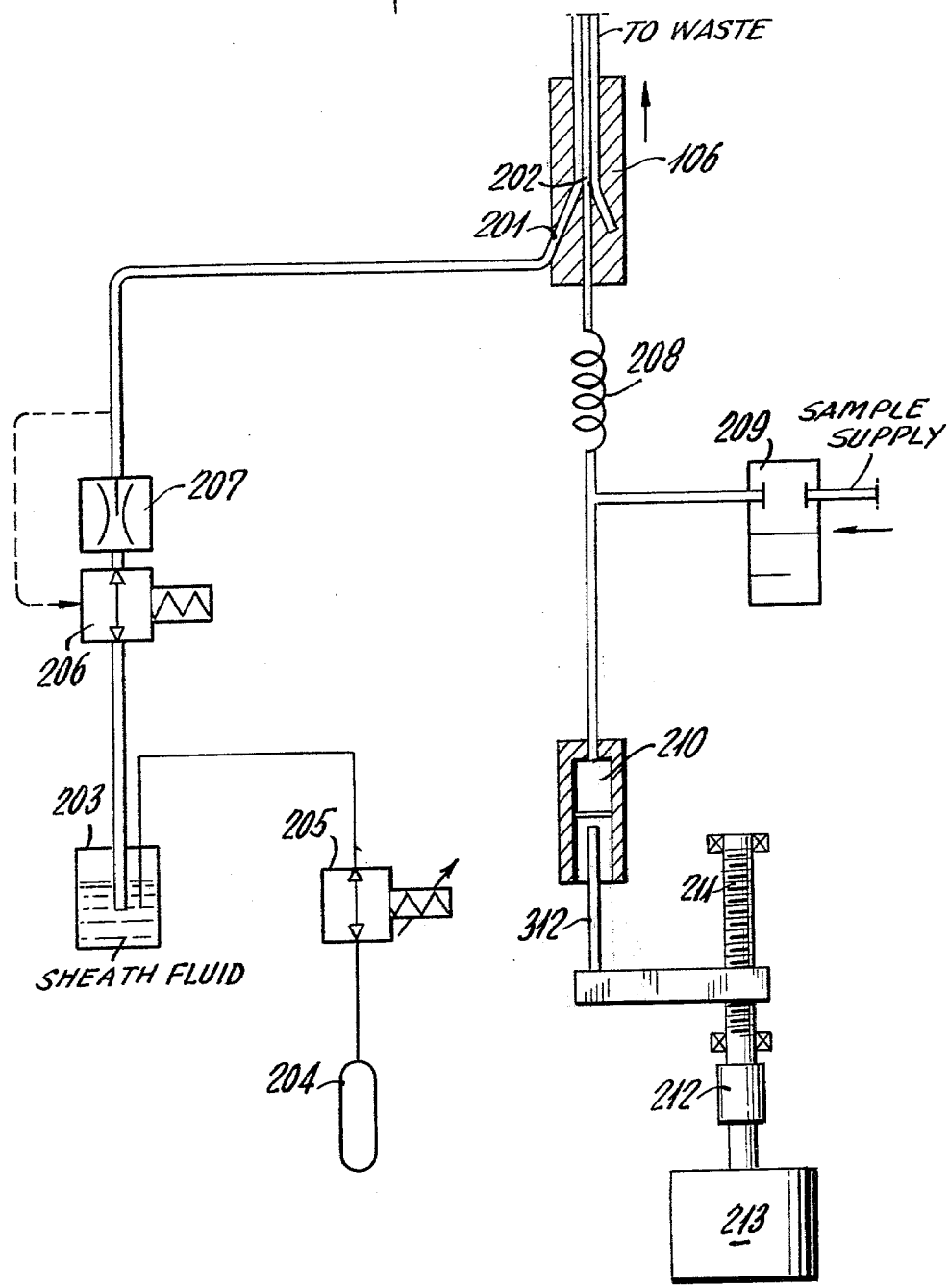

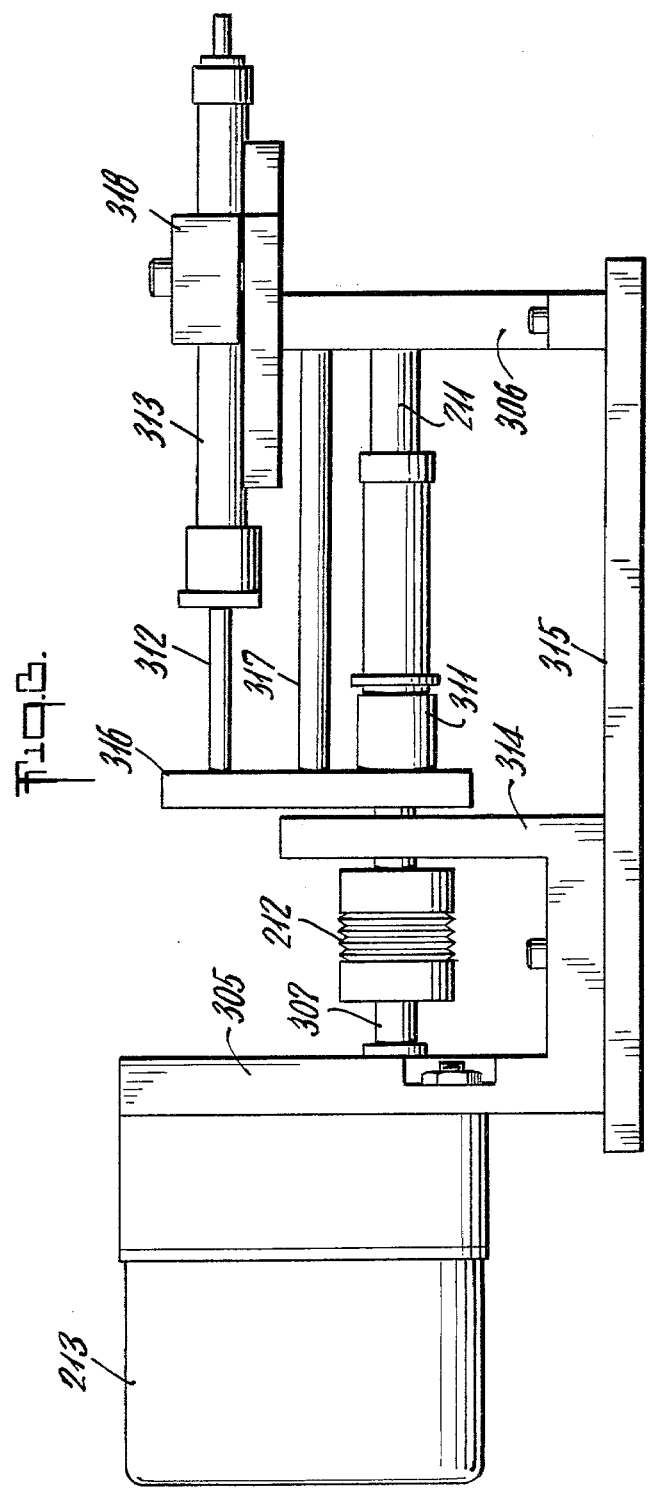

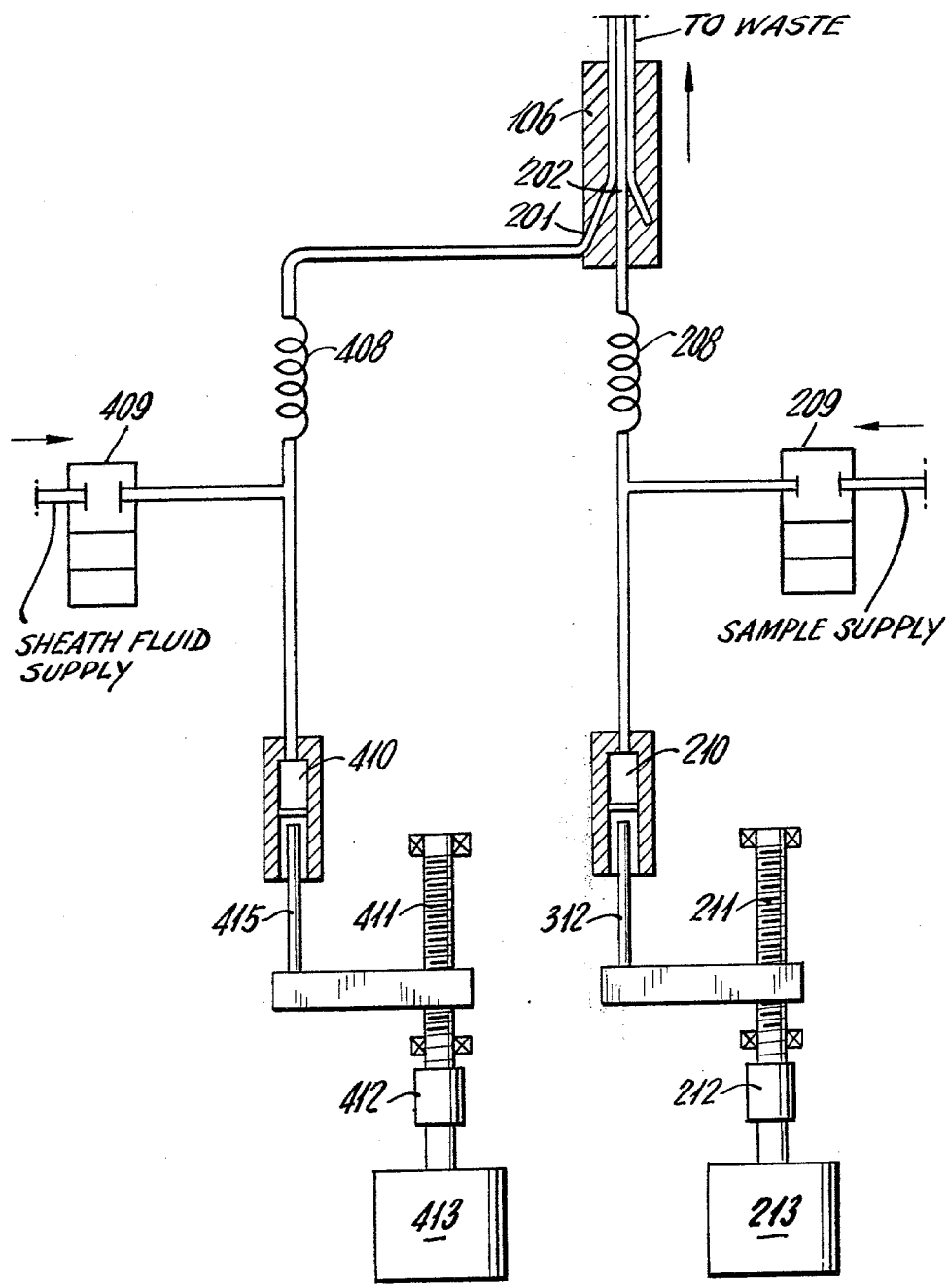

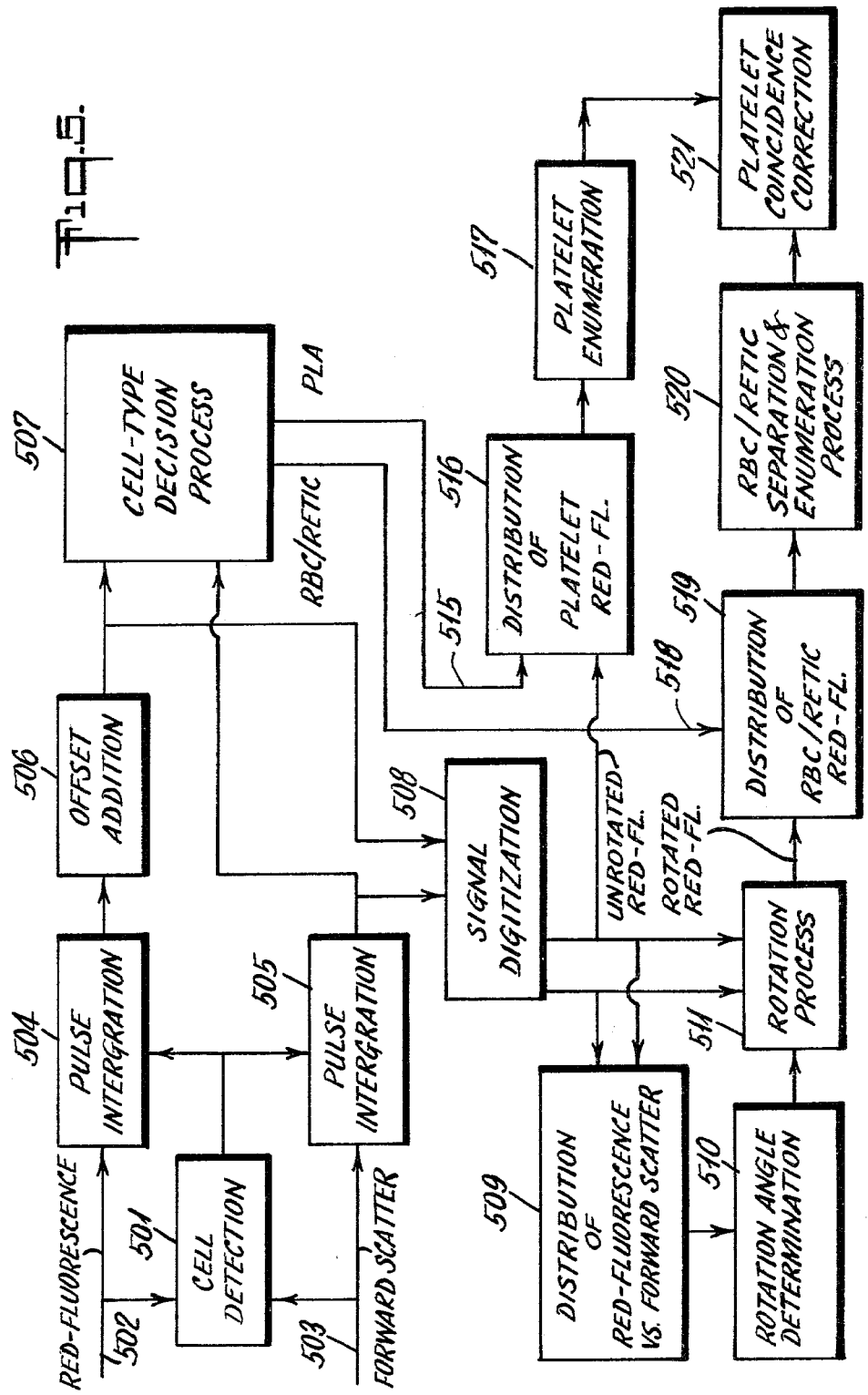

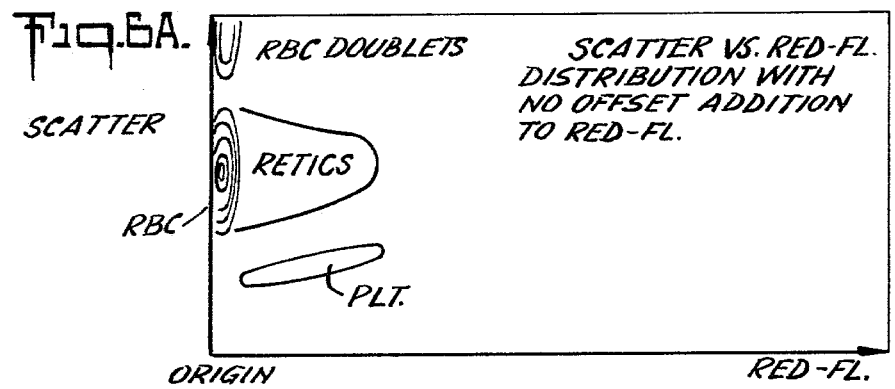
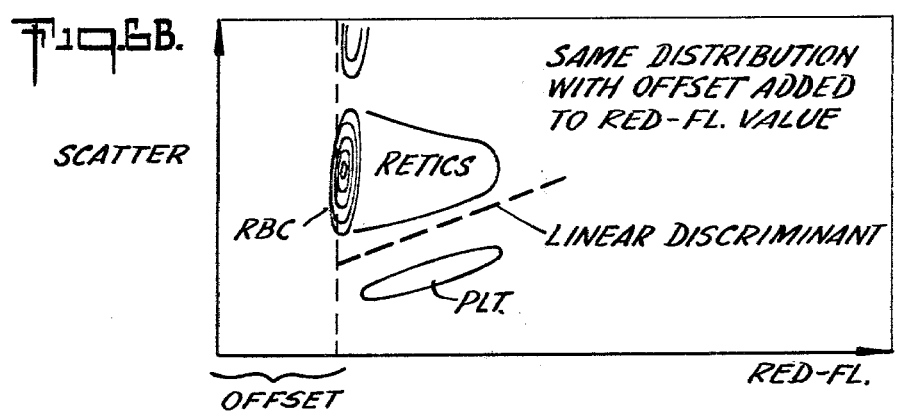
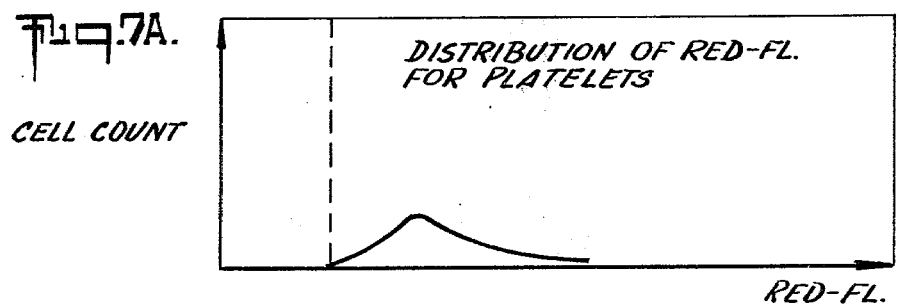
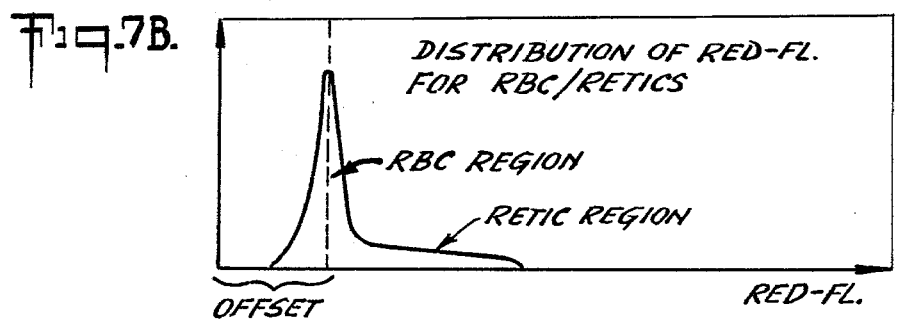

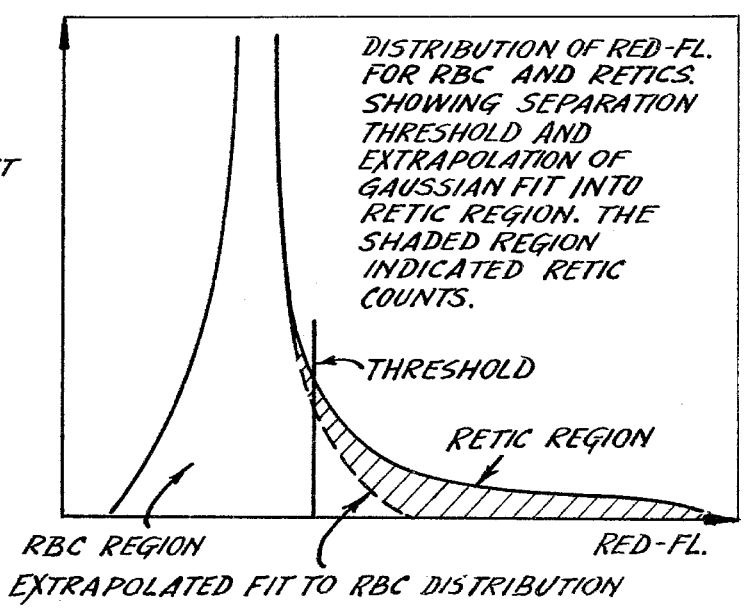

AUTOMATED DETECTION OF PLATELETS AND RETICULOCYTES IN WHOLE BLOOD

FIELD OF THE INVENTION

This invention relates to the automated analysis of blood cells, and more particularly to automated approaches for identifying and enumerating platelets and reticulocytes.

BACKGROUND OF THE INVENTION

Detection and enumeration of reticulocyte cells has provided extensive challenge to designers and manufacturers of automated hematology instruments. Reticulocytes are precursors to red blood cells, and hence the term reticulocyte embraces the evolution and development of the cell whereby the red blood cell is generated. Hence, a cell which is clearly a red cell precursor today will be a red blood cell in a few days more, and will of course mature during the interim. It is, therefore, quite difficult to define objective criteria whereby reticulocytes may be effectively discriminated from red cells. Correspondingly, criteria which have heretofore been developed tend to involve quite subjective interpretations, whereby even the most meticulous manual counts, for example utilizing microscopic optical scanning techniques, will yield results of moderate to extensive disparity.

It is an object of the present invention to provide an automated, effective, highly repeatable approach to discrimination of reticulocytes from red blood cells.

An approach to automated hematology which is increasingly finding acceptance as the preferred approach is one often designated as optical flow cytometry. Such systems employ a hydrodynamically focused channel through which blood cells are passed extremely rapidly, one at a time. The constriction of the channel is illuminated by precisely focused light, for example coherent radiation from a laser. Much can be determined by analysis of light scattered by the cells, and if the blood sample has been treated with specific staining agents, still more can be determined by suitable analysis of fluorescent light stimulated from a stained cell or other fluorescent material passing through the focusing zone.

It is an object of the present invention to utilize the principles of optical flow cytometry automatically and repeatably to identify and enumerate platelets, reticulocytes, and red blood cells in a whole blood sample.

SUMMARY OF THE INVENTION

In accordance with the principles of the present invention, a whole blood aliquot, and typically quite a small one, is treated with acridine orange reagent to stain at least the reticulocytes and platelets, and the sample is passed through an optical flow cytometry flow cell having a substantially narrowed hydrodynamic focal region. Red fluorescent light and forward scattered light are sensed, and based on threshold comparisons, occurrence of a cell in the focal region is noted. A level shift allows characterization of fluorescence related noise, whereupon platelets are discriminated from reticulocytes and red cells based on identification criteria which are a linear function of detected scattered light and detected red fluorescent light (i.e. a straight line threshold in a scatter versus red fluorescence histogram). Thereupon, an orthogonality correction is conducted as to scatter data of individual cells based on fluorescent light detected from the same cell (i.e. coordinate rotation), whereupon a threshold level is developed effectively to separate the red cells from reticulocytes.

DESCRIPTION OF THE DRAWINGS

FIG. 1 shows a stylized version of a commercially available flow cytometric apparatus, which may be adapted for utilization in accordance with the principles of the present invention.

FIGS. 2, 3, and 4 show pump systems whereby sample fluid stream dimensions in the flow cell are narrowed considerably, enabling operation in accordance with the principles of the present invention.

FIG. 5 shows in functional block diagrammatic form a system for processing scattered light and fluorescence emissions in order to discriminate and enumerate platelets and reticulocytes in accordance with the principles of the present invention.

FIGS. 6A and 6B, and 7A and 7B, 8A and 8B and 9 show various histograms illustrating sequences of operation for the embodiment of FIG. 5 in accordance with the principles of the present invention.

BEST MODE FOR CARRYING OUT THE INVENTION

Referring first to FIG. 1, there is shown a stylized functional and structural representation of apparatus which may be utilized in accordance with the principles of the present invention. In fact, the apparatus of FIG. 1 depicts a particular system available commercially under the trade designation CYTOFLUORO-GRAPH®, which is sold by Ortho Instruments, 410 University Avenue, Westwood, Mass. 02090. The apparatus of FIG. 1 incorporates the principles of flow cytometry for cell analysis, and includes capacity for sensing fluorescent response of cells to specific types of illumination.

Focal to the FIG. 1 apparatus is a flow channel 106, wherein cells in liquid suspension are passed, in single file and at a rapid rate (e.g. 2500 cells per second) through a sensing zone. The sensing zone is defined by the intersection of cell flow and an incident light beam, typically focused coherent light from a gas laser. As the cell passes through the sensing zone, it interacts with incident light in a variety of ways. Some light, of course, is absorbed by the cell, other light is scattered at relatively narrow angles to the axis of incident light, and still other light is scattered at angles quite divergent from the axis of incident light, for example at right angles to the incident light.

Furthermore, depending upon the nature of the cell itself, and any dyeing or staining to which the cell may previously have been subjected, fluorescence emissions may occur.

Accordingly, photosensors located at various orientations with respect to the cell stream and the incident laser light permit detection of a unique set of responses for each given type of cell. Thus FIG. 1 includes an argon ion laser 101 and a helium neon laser 102, with the coherent light emitted by each being variously deflected via mirrors 103 and 104 and a lens 105 to the sensing zone of the flow channel 106. As is known in the art, the cell sample stream is carried in laminar fashion within a flowing fluid sheath, to insure that but a single cell will be illuminated in the sensing zone at a given time. Hence, as each cell is illuminated by light from the lens, interaction of the cell with the light may be sensed.

As shown in FIG. 1, an extinction sensor 108 detects the amount of light blocked by the cell, and forward light scatter is detected by photosensors 109 and 110 approximately in a cone of half-angle 20°. Electrical signals generated by the sensors 108, 109 and 110 are coupled to amplifiers 120 and 121, which present electrical signals of suitable amplitude and the like for subsequent analysis and/or display.

In the apparatus of FIG. 1, light which is emitted from the cell by virtue of a fluorescence response is sensed at right angles both to the direction of cell flow and to the axis of incident light. A spherical mirror 125 and a condenser lens 107 collects this light approximately in a cone of half-angle 20°, and couples this light through an aperture 111, successively to a dichroic mirror 112 and to a second mirror 113. A first color filter 114 (e.g. to pass relatively long wavelength light) conveys select light from the dichroic mirror 112 to photosensor 117 (e.g. photomultiplier tube). A second filter 115 selectively passes light of a different color (e.g. relatively short wavelength light) from the second mirror 113 to a second photosensor 116. Electrical signals from sensors 116 and 117, in the form of pulses corresponding to light from respective cells, are coupled to amplifiers 118 and 119, thereby also to produce signals which are adapted for suitable processing.

As shown in the FIG. 1 embodiment, a sensor selector 122 generates output histograms utilizing signals from the amplifiers 118 through 121. For example, one useful form of output is a plot of amplitude of red fluorescence, from sensor 117, against amplitude of green fluorescence, from sensor 116. Such a histogram is shown at display 123, with each point on the histogram representing an individual cell. Clusters or aggregates of points on the histogram represent groups of cells of similar type. Quite evidently, those of ordinary skill in the art find it useful variously to generate histograms of narrow forward angle scatter versus intensity of green fluorescence, narrow forward angle scatter versus axial light extinction, and so forth.

In accordance with the principles of the present invention, it is highly desirable severely to constrict the cross-section of the sample fluid stream at the focal point of the flow channel 106, for example from the more common 20 microns or so in cross-section, down essentially to the cell size of 6 to 7 microns or so. Such narrow fluid stream vastly reduces the noise emergent from the irradiated sample, and hence renders considerably more practical the proposition of making the measurements and discriminations called for in accordance with the principles of the present invention. That is, it will be appreciated that noise as a function of spurious matter passing through the focal point of the fluid stream occurs roughly in proportion to the radius of the stream. Such is also the case with respect to fluorescence related noise, due at least in part to free stain in the stream. Hence the desirability of reducing the fluid stream dimension as much as possible, while still accomodating the cells under examination.

Conventionally, flow cytometry systems have employed a pressure system for delivering sheath fluid and sample fluid into the flow channel. The stream narrowing criteria established for the present invention is easily achieved utilizing a precision sample pump for delivery of sample fluid, and a differential pressure regulator and associated restricter for regulation of the flow of pressure driven sheath fluid. A preferred configuration, which also is the subject matter of concurrently filed application U.S.S.N. 178,489 of J. G. O'Connell entitled "Controlled Hydrodynamic Flow in Flow Cytometry Systems", is shown in FIGS. 2, 3 and 4.

Referring to FIG. 2, there is shown symbolically a flow cell assembly 106 wherein a fluid sheath 201 surrounds a sample fluid flow 202. Such constructions are well-known to those of ordinary skill in the art. Sheath flow is provided from a sheath fluid supply bottle 203, which is pressurized from an air pressure supply 204 via an air pressure regulator 205. Sheath fluid from the bottle 203 passes to a differential pressure regulator 206 and a temperature controlled restriction 207 which the regulator 206 controls. A constant pressure drop therefore is maintained across the restricter 207, irrespective of pressure changes either up or down sheath flow stream. The result is a constant mass flow rate of sheath fluid 201 through the cell 106.

Sample is supplied through a valve 209, and is pressurized by a precision gas tight syringe 210 whose plunger 312 displaces the sample fluid volume. The plunger 312 is stroked by a precision lead screw 211, driven by a permanent magnet synchronous gear motor 213 in conjunction with a universal coupling 212. The sample fluid 202 enters the flow cell assembly 106 from a fluid damper 208.

The development of flow within the cell is obtained by first supplying pressure to the sheath fluid supply bottle 203. Once the mass flow rate of the sheath fluid is established, sample fluid is injected into the system through the sample valve 209. The sample fluid is, in turn, metered through the damper 208 and into the flow cell 106 as the syringe plunger 210 is displaced by operation of the motor 213 and 211. The result is a sample fluid stream 202 encased by sheath fluid 201 in the flow cell 106. The linear velocity of the sample fluid is determined solely by the sheath fluid mass flow rate, while the mass flow rate of the sample fluid is determined solely by the displacement of the sample pump. The sample fluid stream, within the flow cell, has dimensions determined by both the velocity and mass flow rate of the sample fluid. The system thus produces a sample fluid stream of very small dimension which is uniform and constant over time.

FIG. 3 shows a cross-sectional view of a preferred configuration for the motor 213, coupling 212, screw 211 and syringe 210. Support members 305, 306, and 314 are mounted to a base 315, and thereby establish relative spatial relationships between the respective parts. A synchronous motor 213 is affixed to the leftmost upright support 305, and the motor drive shaft 307 meets a universal coupling 212, which in turn drives the precision lead screw 211 between brackets 306 and 314. A rail 317 is carried between support members 306 and 314 intermediate the lead screw 211 and syringe 210, and a lead screw nut 311 is connected to a trolley 316, which rides on rail 317 and, on the opposite side thereof is connected to syringe plunger rod 312. The plunger 312 is matable within the syringe barrel 313.

It will therefore be seen that rotational motive force from synchronous motor 213 is transferred by coupling 212 to the lead screw 211. As lead screw 211 is turned, the lead screw nut is translated thereupon, and correspondingly the syringe plunger 312 is moved into or out of the syringe barrel 313.

FIG. 4 shows an alternative approach to the system set forth in FIG. 2, wherein the sheath fluid line includes a pump means substantially similar to that used in the sample fluid line. Hence, in FIG. 4, the fluid line does not include the differential pressure regulator 206 and restrictor 207, instead employing a motor 413, lead screw 411, and syringe combination 410/415 in similar fashion to the apparatus included in the sample line. Essentially, the FIG. 4 embodiment, like the FIG. 2 embodiment, provides sheath fluid at a constant mass flow rate. The embodiment of FIG. 4, however, by employing an instantly activated motor-pump rather than a thermally responsive pressure regulator and restrictor, as a more rapid start up time. That is, the thermal aspects of the pressure regulator 206 and restrictor 207 of the FIG. 2 embodiment requires several minutes initially to heat up to achieve operational level. The embodiment of FIG. 4 has no such limitation.

Inasmuch as the normal operation of flow cytometry systems requires larger volumes of sheath fluid than sample fluid, the FIG. 4 embodiment no doubt will employ a syringe 410 having a larger volume capacity than the one 210 utilized by the sample fluid line. Likewise, the FIG. 4 embodiment employs separate sheath fluid lines and sample fluid lines which employ respective operating parameters adapted to the desired constant mass flow rate of the respective fluids to be delivered to the fluid cell assembly 106; however, components of the respective lines are functionally analagous to one another in each respect.

In partial summary, then, utilization of the pump and pressure system of FIG. 2 or 4, in conjunction with a system such as shown symbolically in FIG. 1, facilitates processing of whole blood samples in accordance with the principles of the present invention to discriminate and enumerate platelets and reticulocytes.

An important aspect of the principles of the present invention is to provide a suitable stain for platelets and reticulocytes whereby the coupling of focused coherent light to the stained cells will result in emissions of fluorescent light at predictable, controlled wavelengths in order to complete processing in conjunction with scatter measurements, and thereby to discriminate platelets and reticulocytes from one another and from red cells. One such dye is acridine orange.

In a concurrently filed copending application of Peter J. Natale, U.S. Ser. No. 178,481, entitled "Reagent for automated counting of platelets and/or reticulocytes", assigned to the assignee hereof, there is described a preferred reagent for utilization in accordance with the principles of the present invention. The copending Natale application utilizes the dye known as acridine orange, and employs a formulation which takes advantage of the cationic/anionic reaction between acridine orange and ribo-deoxyribo-nucleic compounds. These reactions result in complexes which fluorescent in the red or green wavelength range, when excited with appropriate radiation. Since both platelets and reticulocytes contain forms of ribonucleic compounds, they can be distinguished from other cells and each other by their respective light scatter and fluorescent characteristics, in accordance with the principles of the present invention.

The reagent described by Natale, in order to render the activity of the acridine orange compound relatively optimal, includes paraformaldehyde for stabilization of the cytoplasmic membranes so that natural cell sizes and shapes are maintained, for enhancement of acridine orange entry to and within cell matrices, and for enhancement of the stripping of ribonucleic proteins from the respective nucleic acid for the exposure of additional reactive sites. Additionally, the Natale reagent includes a citrate constituent for chelation of calcium, thus preventing platelet clumping or aggregation, for cationic chelation, thus enhanceing cellular cationic exchange resulting in increased acridine orange entry, for buffering effects near isoelectric pH of interfering proteins, and for maintainance of isotonicity for preservation of cell shape and size.

Thus, for preparation of blood in accordance with the principles of the present invention, and aliquot of whole blood is taken, and at least a portion of the aliquot is provided with adequate amounts of acridine orange stain, preferably in a reagent complex of the type disclosed in the aforementioned Natale application, but alternatively other suitable dye compositions. Thus, as the blood sample, having appropriately stained reticulocyte and platelet cells, is coupled to apparatus of the type shown in either FIGS. 2 or 4, and thence to a flow cytometry system of the sort shown in FIG. 1, cell scatter measurements and fluorescence measurements are taken. In a preferred embodiment red florescence is the fluorescence parameter of greatest significance. Processing in accordance with the principles of the present invention may be appreciated upon consideration of the block diagrammatic system setforth in FIG. 5, and the histograms setforth in FIGS. 6A and 6B, 7A and 7B, 8A and 8B, and 9.

Referring, then, to FIG. 5, the red fluorescence signals, for example from sensor 117 and amplifier 119 of FIG. 1, and the forward scatter signals from sensors 109 and 110 and amplifier 120 of FIG. 1, are coupled to a cell detection network 501. It is the purpose of the cell detection network to distinguish presence of the cell in the flow channel 106 from spurious signal which might otherwise be mistaken as a cell. The presence of a cell is deemed to occur when a linear combination of the input parameters, red fluorescence at line 502 and forward scatter at line 503, exceeds a threshold level. Hence, the cell detection network 501 simply includes separate red fluorescence and forward scatter thresholds, the achievement of both of which can occur substantially only by presence of a cell in the illumination zone of the flow channel 106. Since the detection network 501 serves chiefly to eliminate noise, the red fluorescence and forward scatter thresholds will essentially be empirical values, conditioned on the precise design parameters associated with the flow channel being employed, the nature of the dyes being utilized to stain the cells, and the amount of free or uncombined dye passing through the flow channels and thereby subject to the issuance of fluorescent noise. Additionally, the presence of spurious matter in the sheath or sample fluids may contribute somewhat to noise. In practice, establishment of these noise thresholds is neither a difficult nor elaborate procedure, in accordance with the knowledge and ability of those ordinary skill in the art.

When a cell is detected, noise threshold network 501 couples enabling signals to separate pulse integration networks 504 and 505, which, as noted, perform a straightforward integration process, and produce at their outputs an integrated signal representing the area under respective red fluorescence and forward scatter pulses delivered at inputs 502 and 503. The integrated forward scatter signal is coupled directly to an analog to digital converter 508, and also to still another threshold network 507, which as noted conducts a decision process to distinguish certain cell types. The red fluorescence integrated signal is provided with a baseline offset at amplifier 506, and then is coupled both to the analog to digital converter 508 and to the decision network 507. The addition of the baseline offset at amplifier 506 may be appreciated upon consideration of the histograms of FIGS. 6A and 6B. Both histograms represent a plot or distribution of scatter (on the ordinate) versus red fluorescence (on the abscissa). No such histogram is assembled at this point of the operation, but the histograms, as shown, do illustrate the variety of data combinations which may occur. Groupings corresponding to platelets, reticulocytes, red cell doublets, and red cell singlets will be seen, but it will be noted that the red cell singlet distribution is clustered about the ordinate axis, and indeed the presence of the red fluorescence noise, when combined on a cumulative basis, may result in certain red cells having a negative or zero reading unless an offset is added. Accordingly, after integration occurs at 504, the integrated red fluorescence signal is provided at amplifier 506 with a fixed offset which in essence allows for acquisition of the entire distribution of red fluorescent integrals both above and below the baseline integral value. In particular, the offset red fluorescence distribution of red cells and reticulocytes allows accurate statistical procedures to be followed, as discussed hereinafter. The effect of the offset may readily be appreciated upon consideration of FIG. 6B.

A first cell decision process occurs at threshold network 507, in essence distinguishing platelets from either red cells or reticulocytes. In other words, the integrated scatter and red fluorescence signal (which if actually accumulated point 507 would appear as the clusters set forth in FIG. 6B), have a rather distinct aggregation of platelets, well spaced from the remainder of cells. Hence, a linear discriminant (i.e. a linear combination of scatter and red fluorescence factors), will facilitate identification of each forward scatter-red fluorescence combination arriving to decision network 507, as either corresponding to occurrence of a platelet in the flow channel 106, or occurrence of another cell, which may either be a red cell or a reticulocyte, but which in any event is not susceptible to determination at this stage of the procedure.

Again, from consideration from FIG. 6B, it will be noted that there is indeed a considerable disparity from the aggregation of points corresponding to platelets, and those corresponding to the remainder of the cells; hence, identification of a suitable linear discriminant, for any individual system, will be a rather routine matter, given the knowledge that such a discriminant is to be drawn. If a cell's integrated red fluorescence-scatter coordinate places it below the discriminant line, then that combination indicates that the cell is a platelet and its red fluorescence integral is coupled by a line 515 to a memory network 516, which accumulates a cell count versus red fluorescence data in a manner exemplified by the histogram set forth in FIG. 7A. It will be appreciated that the histogram set forth in 7A is constituted by defining a number of levels or channels along the red fluorescence axis, and for each occurrence of a signal on line 515 having a red fluorescence integral within such range, there is an incrementing of the stored cell count for the associated level or channel. Hence, FIG. 7A sets forth a symbolic presentation, in smooth or analog form, of the information stored in memory 516.

In the event that a forward scatter-red fluorescence combination is apprehended by threshold network 507 to be above the linear discriminant shown symbolically in FIG. 6B, indicating that a platelet cell has not been detected (but lacking the ability to determine whether a reticulocyte or red cell has been detected), the integrated red fluorescence pulse is coupled via line 514 to yet another memory 519, which operates as described hereinafter.

Signal digitization occurs at analog to digital converter 508, producing 8 bit digitally encoded representations, on respective output lines 512 and 513, of integrated forward scatter pulses, and offset, integrated red fluorescence pulses.

An appropriate mode of A to D conversion is as follows. When a cell is detected at 501 there is presented at 502 and 503 pulses, which when integrated are each represented as a level equivalent to the area under the associated pulse. By conducting a linear discharge of the integration signal down to zero, a pulse may be formed, with the width of the pulse proportional to the amplitude of the integral. This pulse is then compared with a very rapid (e.g. 40 megahertz) signal, and the duration of the pulse is represented digitally as the number of 40 megahertz cycles which occur during the length of the total pulse. This number is presented at lines 512 and 513 as 8 bit words, i.e. to a granularity of 256 levels.

It is to be noted that the accuracy of the platelet count will depend largely on the purposes for which that count is taken. For example, in a "platelet only" mode, it may be necessary, or desirable, to allow the user substantial discretion in order to have the final platelet count meet the accuracy desired. For purposes of reticulocyte count, however, a much less accurate platelet count is necessary, it being desirable primarily to use the platelet enumeration for purposes for discrimination of reticulocytes, as described hereinafter.

For subsequent assembly of a red-cell/reticulocyte histogram, a rotation correction is to be made based on a preliminary run of signals. In order to establish this first distribution of red fluorescence versus forward scatter, the precision of the digitized red fluorescence and forward scatter signal optionally may be reduced (e.g. from 8 bit to 6 bit). Thereupon, these 6 bit words are passed into a memory 509 (e.g. 64 by 64) which allows for the storage of information corresponding to a red fluorescence versus forward scatter histogram. This data will be utilized as discussed for purposes of evaluating the rotation correction to be had. FIG. 8A, depicts such a histogram of scatter versus red fluorescence, and amply illustrates the need for a coordinate rotation or the like correction process. The upper grouping on the histogram, representing red cell multiplets such as doublets, along with the singlet red cell distribution, is characterized by a positive slope on the scatter versus red fluorescence distribution. Coordinate rotation is therefore desirable for at least two reasons. First, there is need to have the multiplet distribution vertically aligned with the singlet distribution to facilitate curve fitting processes (to be described hereinafter). Secondly there is need to have a single threshold which will amply descriminate between reticulocytes and all red cells, including multiplets.

The 64 by 64 distribution of red fluorescence versus scatter stored in memory 509 may be thought of as having discrete "channels", each memory location representing the intersection of a scatter channel and a red fluorescence channel. A coordinate rotation is best accomplished by investigating the red blood cell distribution through each scatter channel in which it occurs. Generally, it is known that red blood cells will occur within a given scatter range, and this facilitates the investigation considerably. The basic approach is, for each scatter channel in this range, to detect the fluorescence channel having the peak of the distribution, and then, by progressively extending the inquiry to adjacent fluorescence channels, to evaluate the mean red fluorescence for that given scatter channel. Such inquiry is conducted for each of the scatter channels which carry the red blood cells distribution. The aggregate of these separate means are processed, by simply curve fitting procedures, to yield a single straight line (i.e. of the form y=mx+b where x is red fluorescence, b is the y intercept, m is the slope, and y is scatter) which represents the major axis of the red cell distribution. Hence, with respect to a straight vertical axis, the straight line fit also indicates the amount of coordinate rotation which will be conducted. Simple principles of trigonometry likewise enable the evaluation of an angle which characterizes the slope m of the straight line.

It will be appreciated that the entire foregoing procedure, designated only by block 570, could well be embodied by specifically designed, hard wired apparatus including large numbers of registers, encoders, multiplexers, and the like standard digital processing equipment. In fact, however, it is far preferable to conduct these procedures by means of suitably programmed digital computers. Numerous such apparatus are commercially available and in general use; one of particular attraction for use in accordance with the principles of the present invention is available from Data General Inc. under the trade name "Micronova", and features a 32K memory, and thereby the facility to process 16 bit words. Having described preferred rotation correction methods in detail in the foregoing, it will be appreciated that software designers of ordinary skill in the art may, depending upon the operating system being employed, their own desires and facility in terms of utilizing machine language and aspects of the commercial operating system, accomplish the requisite tasks expeditiously. So also could digital hardware engineers ply their skills to fabricate hardwired versions of determination block 510.

Referring back to FIG. 5, then, the foregoing procedures yield an angle through which the reticulocyte, and red cell (singlet and multiplet) distributions are to be rotated. This angle is coupled to the next block, designated "rotation process". In fact, given a rotation angle (or linear correction function), the actual correction is a relatively simple subtraction process.

Meanwhile, once the rotation angle has been evaluated at 510, the data in memory 509, which was utilized for evaluation of the angle, is less relevant. That is, while it may or may not be desirable further to utilize such data, the essential evaluations to be made in accordance with the principles of the present invention relate to a conduct of the rotation process with respect to digitized red fluorescent signals, and the accumulation of a one dimensional (i.e. cell count versus red fluorescence) distribution of red blood cells and reticulocytes.

It may, then, be desirable merely to clear the memory 509 once the correction criteria have been developed. As shown in FIG. 5, the digitized 8 bit word is subjected at 511 to a rotation correction, and thence is passed to a memory 519 which assembles data representing a cell count versus red fluorescence histogram of the combined red blood cells and reticulocyte counts.

On the subject of the rotation itself, it will be noted that a rotation as such, on a scatter versus red fluorescence distribution, entails a correction with respect to both axes. That is, in a true polar rotation, there will occur both an x and y correction, although in accordance with the principles of the present invention, the y correction may indeed be small. Hence, in FIG. 5, the process is broadly characterized, it being understood that the degree of attention to the x and y amplitude shifts, will vary in accordance with the needs of the designer, and the speed of the available processing apparatus. Indeed, some may wish not to perform strict rotation, instead performing only an approximated shift in parallel to the desired major axis. Such options are well within the purview of the principles of the present invention.

Once the RBC/retic count versus red fluorescence distribution is assembled in memory 519, it is appropriate to separate the red blood cell count from the reticulocyte count. FIGS. 7B and 9 represent the data stored in Memory 519.

The principle source of noise in a system such as utilized in accordance with the principles of the present invention, and generally characterized in FIG. 1, is the sample stream itself. That is, as discussed hereinbefore, extreme noise may arise from spurious matter, uncombined fluorescent dyes or materials, and the like in the stream. Essentially, this "white" or Gaussian noise, and accordingly the data in Memory 519, in part mimics a Gaussian curve, including the actual contribution of the irradiated red cells, if any, and the noise generated attendant to fluorescence generated from the stream.

Hence a preferred rationale for discriminating red blood cells from reticulocytes is to fit a Gaussian curve to the lower of leftmost portions of the FIG. 9 distribution, and once a proper Gaussian curve has been fit to that data, to conduct statistical inquiries, progressively rightwardly along the red fluorescence channels, to determine the point at which the actual cell count curve begins to diverge substantially (i.e. within given statistical criteria) from the Gaussian curve. Such point is deemed a nominal threshold between all red blood cells and reticulocytes. Above this threshold, then, one may extrapolate the Gaussian curve to account for the balance of red cells; excluding these, all other cells above the threshold are safely deemed reticulocytes.

In greater detail, the process is performed as follows, reference being made to FIG. 9 for purposes of clarification. In fact, FIG. 9 is a symbolic depiction of data stored in Memory 519 of FIG. 5.

First, the "mode" or fluorescence channel having peak red cell count is identified. Thereupon, count data in all channels to the left of the mode may be utilized to develop a Gaussian curve which best fits the "half distribution", which curve will be employed for the later half of the distribution. Thereupon, for each channel beyond the mode and in sequence, the developed curve is extended to find the count which would result were the cell counts in the channels to follow a precise Gaussian distribution. For each such channel, it is preferred to conduct statistical test to determine the degree to which the actual count for the channel diverts from the Gaussian calculation. Such fitting and comparison steps occur sequentially, red fluorescence channel by red floresence channel, above the mode of the distribution. A threshold is deemed to be found whenever a comparison yields a difference from the expected or Gaussian point, which exceeds the predetermined statistical standards.

Once the threshold has been established, the count in each channel therebeyond will have a red cell component indicated by the extrapolated Gaussian curve, and a reticulocyte component, based on the difference between that extrapolated curve and the actual count in the channel. In fact, viewing FIG. 9, it will be noted that the Gaussian contribution (i.e. red blood cells) quickly vanishes above the threshold.

It will be appreciated that the threshold level, being selected as a function of statistical criteria, will no doubt be recognized as a point slightly after some reticulocytes have been embodied in the counts. It may, accordingly, be desirable to "back off" by a number of channels, determined by the designer, in order to pick up a few reticulocytes which, prior to statistical identification of the threshold, were dismissed as statistical aberration.

In FIG. 5, the foregoing operations are embodied in block 520, which like block 510, is embodied as a suitably programmed computer system, or as a specially designed hardwired mechanism.

It will be appreciated that the literature includes numerous curve fitting approaches and techniques whereby a wide variety of curves, including Gaussian functions, may be fit to given collections of data. Indeed, software packages are commercially available for such curve fitting operations. The principles of the present invention are not directed per se to such a purely mathematical formula, and are not intended to appropriate such purely mathematical processing. Rather, it is contemplated in accordance with the principles of the present invention that these mathematical formulae, which are taught throughout the literature, may be employed advantageously (so long as they may be accommodated by the memory, speed, and the like parameters of the hardware system being employed) in order to discriminate the types of cells being studied in accordance with the principles of the present invention. Likewise, numerous statistical tests are available when conducting the channel by channel Gaussian fit versus actual count comparisons. One such test which has been found suitable is the Chi square test (one degree of freedom), but it will be appreciated that numerous others may also be appropriate.

Therefore, total reticulocyte and red cell counts are evaluated at 520, and the respective counts coupled for a final coincidence correction based upon the platelet counts.

The significance of the platelet correction may be appreciated by considering FIG. 4A, together with the following precepts. First, viewing FIG. 4A, it will be noted that the reticulocyte aggregation likely has a scatter parameter which is in the same range as that for a red blood cell, but is distinguished therefrom based on divergent red fluorescence ranges. The reticulocytes also, however, have a red fluorescence value roughly equivalent to that of platelets, and are distinguished therefrom based largely upon divergent scatter ranges. It is to be noted, however, that platelets and red cells could possibly reside in the sample stream so closely to one another that a red cell forward scatter signal and a platelet red fluorescence signal might, from the standpoint of system dynamics, be issued at substantially the same time. Hence, there would be seen by the system a forward scatter-red fluorescence combination which would indicate a reticulocyte in the channel, rather than a coincident red cell-platelet event. The platelet coincidence correction avoids, on a statistical basis, error attendant to this phenomenon. Essentially, the platelet coincidence correction at 521 is conducted by reducing the reticulocyte count developed at 520 by a factor equivalent to the likelihood of a platelet-red cell event occurring.

Perhaps exemplary numbers will illustrate this point. Assuming a cell sample having raw (i.e. uncorrected) counts of n red cells, 0.01 n reticulocytes, and 0.05 n platelets, with the system operating at such a rate that at any given time there is a probability p that any cell is present. In such a situation, there is substantially 0.05 p likelihood of a coincidence of platelet and a red cell. In such event, the platelet correction at 521 would be accomplished by reducing the reticulocyte count by 0.05 p. Generally, for systems reasonably within the contemplation of the principles of the present invention, the factor "p" may be in the range of of 2 to 3 percent. Hence the platelet coincidence correction may not be required for certain applications.

It will be appreciated that the foregoing has set forth preferred and illustrative embodiments of the principles of the present invention, but that numerous alternative embodiments may occur to those of ordinary skill in the art without departure from the spirit or scope of the present invention.

We claim:

1. A method of identifying and enumerating platelet and reticulocyte cells in whole blood comprising the steps of:
   (a) providing an aliquot from the blood to be studied;
   (b) staining at least the reticulocyte and platelet cells of said aliquot with an acridine orange reagent;
   (c) passing at least a portion of said aliquot, substantially a cell at a time through an area of focused optical stimulation, said area having a cross-sectional dimension comparable to the expected dimension of red cells;
   (d) detecting light scattered by, and fluorescent light stimulated from cells in said area;
   (e) identifying platelet identification criteria as a linear function of detected scattered light and detected fluorescent light;
   (f) discriminating platelets from reticulocytes and red blood cells based on said identification criteria;
   (g) providing an orthogonality correction at least as to fluorescent light detected from individual cells, based on scatter and fluorescent light detected from the cells;
   (h) defining fluorescent light threshold criteria separating red cells from reticulocytes; and
   (i) identifying as reticulocytes those cells, platelets excluded, detected as issuing fluorescent light greater than said threshold criteria.

2. A method as described in claim 1 wherein said step of providing an orthogonality correction comprises the steps of:
   (a) assembling a scatter versus fluorescence distribution at least for red cell singlets and multiplets;
   (b) characterizing said red cells as a linear function of scatter and fluorescence; and
   (c) correcting the fluorescent light coordinate of cells in said distribution by a correction proportional to said linear function.

3. A method as described in claim 2 and further including assembling reticulocyte cell data in said distribution, and wherein said correcting step includes identical correction for said reticulocyte cell data.

4. A method as described in claim 2 or claim 3 wherein said characterizing step includes evaluating the angular disparity between said linear function and the scatter axis of said distribution, and wherein said correcting step includes providing a radially constant, polar correction of fluorescence and scatter coordinates of cells of said distribution, as a function of said angular disparity.

5. A method as described in claim 1, and further including the step of excluding platelet fluorescence and scatter data from said correction step and steps subsequent thereto.

6. A method as described in claim 1 wherein said defining step comprises the steps of:

(a) assembling a distribution of red and reticulocyte cells versus associated fluorescent light stimulations;
(b) identifying the peak of said distribution;
(c) fitting a Gaussian curve to the portion of said distribution below said peak; and
(d) detecting the fluorescent level at which said distribution, above said peak, deviates from said Gaussian curve by a predetermined statistical function, said detected level being the basis for said threshold criteria.

7. A method as described in claim 1 wherein said threshold criteria comprise adoption of said detected fluorescent level as a nominal threshold between red cells and reticulocytes, and providing predetermined correction to cell counts on at least one side of said threshold as a function of said Gaussian curve and said statistical function.

* * * * *